United States Patent [19]

Rorvig

[11] 4,003,993
[45] Jan. 18, 1977

[54] PIGLET ENTERITIS TREATMENT

[75] Inventor: Knud Rorvig, Gentofte, Denmark

[73] Assignee: Biofac A/S, Copenhagen, Denmark

[22] Filed: Dec. 15, 1970

[21] Appl. No.: 98,479

[30] Foreign Application Priority Data

Dec. 15, 1969 Switzerland .................. 18597/69

[52] U.S. Cl. ............................................ 424/104
[51] Int. Cl.$^2$ ........................................ A61K 35/38
[58] Field of Search ...................... 424/104, 94

[56] References Cited

UNITED STATES PATENTS 2,906,621  9/1959  Catron ................................. 424/94

FOREIGN PATENTS OR APPLICATIONS 150,202  1/1962  U.S.S.R. ............................ 424/104

OTHER PUBLICATIONS

U.S. Dispensatory–25th edit.(1955), pp. 965, 1017 and 1018.

Hawk et al.—Practical Physiological Chemistry—12th edit.—1947—pp. 317 to 321.

*Primary Examiner*—Sam Rosen
*Attorney, Agent, or Firm*—Beveridge, DeGrandi, Kline & Lunsford

[57] ABSTRACT

The therapeutic composition of the invention comprises an extract obtained from the contents of at least a portion of that section of the digestive system of a ruminant consisting of the rumen and the section of the alimentary canal immediately successive to the rumen, said extract being sterilized.

The invention above includes a method of producing such compositions which comprises forming an extract of the contents of this said portion of the digestive system of a ruminant and sterilizing the extract. The invention also includes a method of treating enteric diseases in non-ruminants which comprises administering to the non-ruminant the therapeutic composition of this invention.

14 Claims, No Drawings

PIGLET ENTERITIS TREATMENT

As is known, one of the prime economic problems arising from the breeding of pigs, is the rather high death rate among the piglets during the first weeks of their life, caused by enteric diseases.

The precise reason for such outbreaks of enteritis has been the subject of very much discussion. In many cases such outbreaks occur as the result of the wrong type of nutrition and it has also been proposed that insufficient warmth may contribute to such outbreaks which are often fatal to the animals concerned.

However, it seems that the said causes are only one side of the problem, as they very likely do not cause a fully developed pathological picture with diarrhoea etc. until the digestive systems of the piglets are already impaired because of a change in the bacterial flora of the alimentary canals of the piglets. Such a change may be due to the lack of certain nutritional elements of more or less vitamin-like character.

It is an object of the present invention to provide a therapeutic composition which assists in maintaining normal bacterial conditions in the alimentary canal of non-ruminants.

It is a further object to provide method of producing such compositions.

Yet a further object is the provision of a method of treating enteristic diseases in non-ruminants. Comprehensive examinations with a view to procuring such means have led to the composition of the present invention.

The composition of the invention comprises a therapeutic composition useful in the treatment of enteristic diseases in non-ruminants which comprises an extract obtained from the contents of at least a portion of that section of the digestive system of a ruminant consisting of the rumen and the section of the alimentary canal immediately successive to the rumen, said extract being sterilized.

The invention also comprises a method of manufacturing an extract or a concentrate of the invention which comprises forming an extract of the contents of the rumen and/or the part of the alimentary canal of ruminants in immediate succession to the rumen and sterilising the extract. The sterilization may be effected by heat treatment or by autoclaving the extract, most preferably at pH values greater than 7, or by physical irradiation or by admixture of adequate disinfectants as for instance methyl p-hydroxybenzoate (Nipagines). The extract is preferably admixed with a suitable carrier or diluent which may be an absorbant to facilitate dispensing of the product.

The extract is preferably concentrated before being admixed with a suitable carrier or diluent and may if desired be dried and the dried product admixed with the carrier or diluent. The composition may also contain other ingredients of a therapeutic or diethetically active nature.

It is known, for instance for the Swiss Patent No. 463,931 that the biological value of a mixed feed for ruminants may be improved by the admixture therewith of the non-sterilized contents of the rumen obtained from healthy ruminants, i.e. content of rumen containing live bacteria. In contrast, the composition of the present invention contains sterilized extracts, i.e. extracts containing no live bacteria. It is surprising that the composition of the invention has such a distinctly favourable effect on the alimentary canal of nonruminants as appears from the following examples.

EXAMPLE I

This example shows the high degree that it is possible to maintain the normal intestinal flora of piglets. For example animals administered substances manufactured in accordance with this invention had far few cases of enteritis or coli-oedema as well as a smaller death rate that non-treated animals.

PREPARATION OF EXTRACT 500 kg of the rumen content from ruminants were extracted with 500 liters of water. The resulting extract was filtered the extract being passed at least twice through the filter. The filtrate obtained was concentrated under vacuum to a volume of 15 liters and the concentrate then heated for 30 minutes at 127° C.

265 piglets were picked out for experiments. They were all taken from the sow when they were 50 days old. They were divided into a control group of 78 pigs and three treatment groups in a total of 187 pigs.

*Treatment group A* comprised 53 pigs which got each 3 g of a protein mixture containing 2% rumen juice extract. 29 pigs got coli-oedema, hereof died 2, 24 remained healthy.

*Treatment group B* comprised 65 pigs which got each 4 g of the above preparation containing 2% rumen juice extract. Hereof 28 got sick and 1 died. The other 37 remained healthy.

*Treatment group C* comprised 69 pigs which got each 5 g of the above preparation. Hereof 24 got sick, but none of them died. The other 45 remained healthy.

| Daily: Protein mixture with 2% rumen juice extract | Number | Sick Total % | | Dead Total % | | Dead % of sick | Healthy Total % | |
|---|---|---|---|---|---|---|---|---|
| Control group | 0 | 78 | 44 | 56 | 6 | 7,6 | 13 | 34 | 44 |
| | 3 g | 53 | 29 | 55 | 2 | 3,3 | 7 | 24 | 45 |
| | 4 g | 65 | 28 | 43 | 1 | 1,5 | 3,5 | 37 | 57 |
| | 5 g | 69 | 24 | 35 | 0 | 0 | 0 | 45 | 65 |

As appears from the survey it seems that a substance manufactured according to the present invention has outstanding prophylactic qualities against enterites and coli-oedema in piglets.

EXAMPLE II 200 kg content of rumen were extracted with 100 kg of water and the extract treated in a similar manner to that in Example 1 to give 150 kg of extract. After sterilization the extract was dried and 1 kg of dry matter resulted. For the experiment 111 piglets were used ranging in age from 2 to 10 days. The experiment group itself comprised 85 piglets, the other 26 were used for a control. All the 111 piglets had enteritis. The 85 piglets of the experiment group each received for three days running 1 g of a protein mixture containing 2% rumen juice extract. Of the experiment group only 1 died. In the control group 12 piglets out of the 26 died.

EXAMPLE III

The present example comprises the treatment of new-born pigs with preparations according to the present invention. The animals in this example have been taken from herds attacked by E. Coli Dysenteria (epidemic).

A group of 60 piglets served as control, i.e. piglets treated neither with antibiotics nor with a composition according to the present invention.

A group of 7123 piglets were treated with antibiotics (oxytetracycline = neomycin), and finally 7790 piglets were treated with a preparation according to the present invention.

The results are set out in the following table:

| Number of animals | Treatment | Sick | | Dead | | Weight in kg on the 70th day of living |
|---|---|---|---|---|---|---|
| 60 | Control | 26 | 43% | 12 | 20% | 18.6 |
| 7123 | Antibiotics | 2067 | 29% | 780 | 11% | 21.5 |
| 7790 | Preparation acc. to the present invention | 2051 | 26% | 103 | 1.3% | 24.6 |

The preparation according to the present invention was administered in the form of a suspension containing 0.02 g of the preparation which together with 3g skimmed milk powder was stirred into 10 to 20 ml water. The resulting suspension was given intranasally on the piglets' 2nd day of living by therapeutical use on piglets attacked by the disease.

The composition according to the present invention may be administered as a solid or liquid preparation and may contain other therapeutically or dietetically active principles.

I claim:

1. A therapeutic composition useful in the treatment of piglet enteritis which comprises an extract obtained from the contents of at least a portion of that section of the digestive system of a ruminant consisting of the rumen and the section of the alimentary canal immediately successive to the rumen, said extract being prepared by mixing said contents with water, using one to two parts water per two parts of said contents, filtering the mixture, and in arbitrary succession sterilizing by heating and concentrating the filtrate by evaporation to obtain a concentrated extract.

2. A therapeutic composition as claimed in claim 1 in which the extract is in admixture with a carrier therefore.

3. A therapeutic composition as claimed in claim 1 which also contains at least one other ingredient selected from therapeutically active materials.

4. A therapeutic composition as defined in claim 1, wherein said concentrated extracted is concentrated to dryness.

5. A therapeutic composition useful in the treatment of diseases having the characteristics of enteritis in nonruminants as claimed in claim 1, wherein said extract is obtained from the chewed normal cattle feed contained in the rumen and the section of the alimentary canal immediately successive to the rumen of a newly slaughtered ruminant.

6. A method of producing a therapeutically active extract useful in the treatment of piglet enteritis which comprises forming an extract from the contents of at least a portion of that section of the digestive system of a ruminant consisting of the rumen and the section of the alimentary canal immediately successive to the rumen; said extract being prepared by mixing said contents with water, using one to two parts water per two parts of said contents, filtering the mixture and in arbitrary succession, sterilizing by heating and concentrating the filtrate by evaporation to obtain a concentrated extract.

7. A method as claimed in claim 6 in which the extract is first concentrated before being sterilized.

8. A method as claimed in claim 6 in which the aqueous extract is dried to produce a solid product.

9. A method of producing a therapeutically active extract useful in the treatment of piglet enteritis as claimed in claim 6 wherein said extract is obtained from the chewed normal cattle feed obtained in the rumen and the section of the alimentary canal immediately successive to the rumen of a newly slaughtered ruminant.

10. A method of treating piglet enteritis which comprises orally administering to the animal a therapeutic composition comprising an extract obtained from the contents of at least a portion of the digestive system of a ruminant consisting of the rumen and the section of the alimentary canal immediately successive to the rumen, said extract being prepared by mixing said contents with water, using one to two parts water per two parts of said contents, filtering the mixture, and in arbitrary succession sterilizing by heating and concentrating the filtrate by evaporation to obtain a concentrated extract.

11. A method as claimed in claim 10 in which the composition also contains at least one other ingredient selected from therapeutically active materials.

12. A method of treating piglet interitis as claimed in claim 10, wherein said extract is obtained from the chewed normal cattle feed contained in the rumen and the section of the alimentary canal immediately successive to the rumen of a newly slaughtered ruminant.

13. A method of preventing piglet enteritis which comprises orally administering to the animal a prophylactic composition comprising an extract obtained from the contents of at least a portion of the digestive system of a ruminant consisting of the rumen and the section of the alimentary canal immediately successive to the rumen, said extract being prepared by mixing said contents with water, using one to two parts water per two parts of said contents, filtering the mixture, and in arbitrary succession sterilizing by heating and concentrating the filtrate by evaporation to obtain a concentrated extract.

14. A method of preventing piglet enteritis as claimed in claim 13, wherein said extract is obtained from the chewed normal cattle feed contained in the rumen and the section of the alimentary canal immediately successive to the rumen of a newly slaughtered ruminant.

* * * * *